United States Patent [19]

Parg et al.

[11] Patent Number: 4,744,812

[45] Date of Patent: May 17, 1988

[54] SUBSTITUTED DIPHENYL ETHERS, HERBICIDES CONTAINING THESE COMPOUNDS AND THEIR USE AS HERBICIDES

[75] Inventors: Adolf Parg, Bad Durkheim; Bruno Wuerzer, Otterstadt; Gerhard Hamprecht, Weinheim, all of Fed. Rep. of Germany

[73] Assignee: BASF Aktiengesellschaft, Ludwigshafen, Fed. Rep. of Germany

[21] Appl. No.: 707,190

[22] Filed: Mar. 4, 1985

Related U.S. Application Data

[63] Continuation of Ser. No. 337,287, Jan. 5, 1982, abandoned.

[30] Foreign Application Priority Data

Jan. 9, 1981 [DE] Fed. Rep. of Germany ....... 3100387

[51] Int. Cl.$^4$ .................... A01N 43/08; C07C 143/68; C07C 147/06; C07C 147/14
[52] U.S. Cl. ......................................... 71/88; 71/90; 71/98; 71/103; 71/105; 71/106; 71/107; 71/109; 71/111; 71/115; 71/122; 71/124; 549/491; 549/496; 549/501; 549/502; 556/416; 556/418; 556/426; 556/423; 556/427; 556/446; 558/44; 558/48; 558/52; 558/406; 558/408; 558/410; 560/9; 560/11; 560/12; 560/15; 560/16; 560/21; 560/60; 560/61; 560/255; 562/426; 562/429; 562/430; 562/435; 562/470; 568/29; 568/30; 568/33; 568/44; 568/49; 568/50; 568/52; 568/585; 568/586; 568/592; 568/635; 568/636; 568/637; 568/638; 568/639
[58] Field of Search .................... 558/44, 48, 52, 406, 558/408, 410; 560/9, 11, 12, 21, 61, 255, 15, 16, 60; 562/430, 435, 426, 429, 470; 568/29, 30, 33, 44, 49, 50, 52, 585, 586, 592, 635, 636, 637, 638, 639; 556/416, 446, 418, 423, 426, 427; 71/88, 90, 98, 111, 115, 103, 105, 109, 107, 106, 122, 124; 549/491, 496, 501, 502; 260/465 F

[56] References Cited

U.S. PATENT DOCUMENTS

3,835,176 10/1976 Matsuo et al. ................. 260/465 D
4,004,914 1/1977 Toepfl ............................... 71/100
4,231,953 11/1980 Henrick et al. ..................... 101/14
4,304,936 12/1981 Rohr et al. ......................... 71/100
4,311,514 1/1982 Szczepanski et al. ............. 71/100

FOREIGN PATENT DOCUMENTS

2013497 8/1979 United Kingdom .
2025952 1/1980 United Kingdom .
1591960 7/1981 United Kingdom .

Primary Examiner—Nicky Chan
Attorney, Agent, or Firm—Keil & Weinkauf

[57] ABSTRACT

Substituted diphenyl ethers of the formula

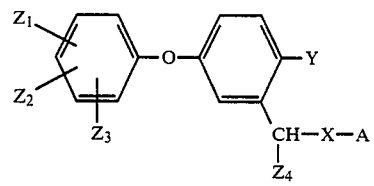

where $Z_1$, $Z_2$ and $Z_3$ are hydrogen, halogen, nitro, cyano, carboxyl, alkyl, haloalkyl, alkoxy, haloalkoxy, alkylmercapto, haloalkylmercapto, alkylsulfinyl, haloalkylsulfinyl, alkylsulfonyl or haloalkylsulfonyl, $Z_4$ is hydrogen, cyano, alkyl, alkoxy, acetoxy or alkylmercapto, Y is hydrogen, halogen, cyano or nitro, X is oxygen, sulfur, sulfinyl or sulfonyl, and A is hydrogen, unsubstituted or substituted alkyl

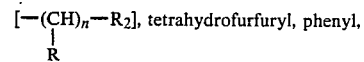

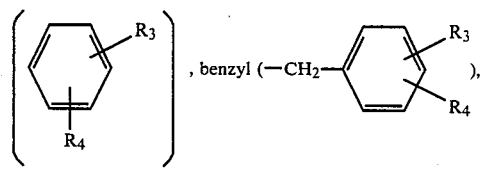

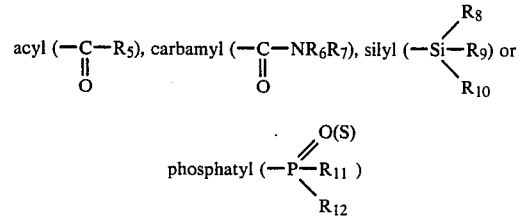

and can also be sulfonyl

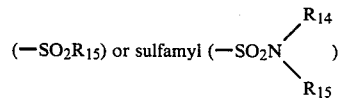

when X is oxygen, and, when $Z_4$ is alkoxy or alkylmercapto, can also be a methylene chain $-(CH_2)_m-$ by which the radicals $Z_4-CH-X-$ are bonded to form a ring, $R_1$ is hydrogen, methyl, ethyl or n-propyl, $R_2$ is cyano, methoxy, ethoxy or

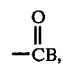

where B is OH, ONa, O—alkyl, unsubstituted or substituted phenoxy, $-NH_2$, $-NH-$alkyl or $-N(alkyl)_2$, n is 1, 2 or 3, $R_3$ and $R_4$ are hydrogen, halogen, methyl, nitro, cyano, methoxy, carboxyl, trifluoromethyl or an O-propionic acid methyl ester group, $R_5$ is methyl, (Abstract continued on next page.)

ethyl, propyl, chloromethyl, dichloromethyl, trichloromethyl, methoxymethyl, phenyl, nitro-substituted phenyl, alkyl-substituted phenyl or α-2,4-dichlorophenoxyethyl, $R_6$ and $R_7$ are hydrogen, alkyl, alkoxyalkyl, dihalophenyl, cyclohexyl or methoxy, $R_8$, $R_9$ and $R_{10}$ are methyl, ethyl, n-propyl or n-butyl, $R_{11}$ and $R_{12}$ are methoxy, ethoxy, thiomethyl, thioethyl, thio-n-propyl, N,N-dimethylamino or N,N-diethylamino, $R_{13}$ is methyl, ethyl, phenyl or trifluoromethyl, $R_{14}$ and $R_{15}$ are hydrogen, methyl, ethyl, n-propyl, isopropyl, n-butyl, n-hexyl, n-heptyl, methoxy, ethoxy or isopropoxy, and m is 2 or 3; and herbicides containing these compounds.

6 Claims, No Drawings

SUBSTITUTED DIPHENYL ETHERS, HERBICIDES CONTAINING THESE COMPOUNDS AND THEIR USE AS HERBICIDES

This application is a continuation of application Ser. No. 337,287, filed on Jan. 5, 1982, now abandoned.

The present invention relates to novel valuable diphenyl ethers, their use as herbicides, and herbicides which contain these compounds as active ingredients.

The use of the sodium salt of 2-chloro-4-trifluoromethyl-3'-carboxy-4'-nitrodiphenyl ether (A) for controlling broad-leaved weeds in soybeans is disclosed in German Laid-Open Application DOS No. 2,311,638. Amongst the known diphenyl ethers, 2-chloro-4-trifluoromethyl-3'-ethoxycarbonyl-methylthio-4'-nitrodiphenyl ether (C) is distinguished by a high herbicidal activity, together with a low phytotoxicity for rice (Japanese Preliminary Published Application No. 77/21,320). Further, the herbicidal properties of 2-chloro-4-trifluoromethyl-3'-methyl-4'-nitrodiphenyl ether (B) are disclosed in German Laid-Open Application DOS No. 2,304,006.

We have found that the novel substituted diphenyl ethers of the general formula I

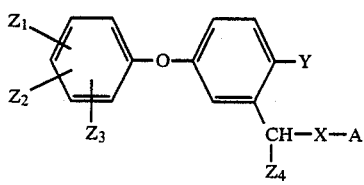

where $Z_1$, $Z_2$ and $Z_3$ are each independently of one another hydrogen, halogen (e.g., fluorine, chlorine or bromine), nitro, cyano, carboxyl, lower alkyl (e.g., methyl), lower haloalkyl (e.g., trifluoromethyl), lower alkoxy (e.g., methoxy), lower haloalkoxy (e.g., trifluoromethoxy), lower alkylmercapto, lower haloalkylmercapto (e.g., trifluoromethylthio), lower alkylsulfinyl, lower haloalkylsulfinyl lower alkylsulfonyl or lower haloalkylsulfonyl (e.g., trifluoromethylsulfonyl), $Z_4$ is hydrogen, cyano, $C_1$–$C_4$-alkyl, $C_1$–$C_4$-alkoxy, acetoxy or $C_1$–$C_4$-alkylmercapto, Y is hydrogen, halogen (chlorine or bromine)*, cyano or nitro, X is oxygen, sulfur, sulfinyl or sulfonyl, and A is hydrogen, $C_1$–$C_6$-alkyl, substituted

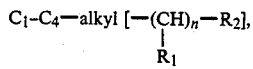

tetrahydrofurfuryl, $C_1$–$C_4$-alkyl-substituted tetrahydrofurfuryl, phenyl, substituted phenyl

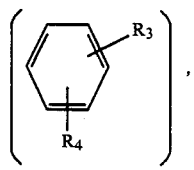

benzyl, substituted benzyl

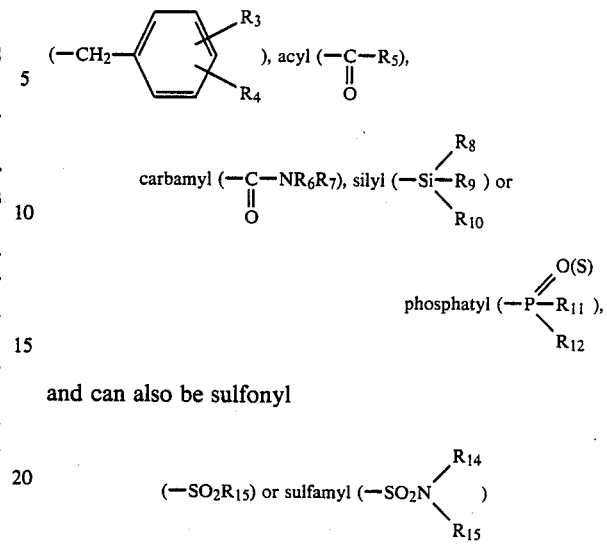

and can also be sulfonyl $(-SO_2R_{15})$ or sulfamyl $(-SO_2N\begin{smallmatrix}R_{14}\\R_{15}\end{smallmatrix})$ when X is oxygen, and, when $Z_4$ is alkoxy or alkylmercapto, A can also be a methylene chain —$(CH_2)_m$— by which the radicals $Z_4$—CH—X— are bonded to form a ring, $R_1$ is hydrogen, methyl, ethyl or n-propyl, $R_2$ is cyano, methoxy, ethoxy or

where B is OH, ONa, $OCH_3$, $OC_2H_5$, O—i—$C_3H_7$ or O—$(C_4$–$C_{20})$-alkyl, O-phenyl, substituted phenoxy, —$NH_2$, —NH—$(C_1$–$C_4)$-alkyl or —$N(C_1$–$C_4$-alkyl$)_2$, n is 1, 2 or 3, $R_3$ and $R_4$ independently of one another are hydrogen, halogen, methyl, nitro, cyano, methoxy, carboxyl, trifluoromethyl or an O-propionic acid methyl ester group, $R_5$ is methyl, ethyl propyl, chloromethyl, dichloromethyl, trichloromethyl, methoxymethyl, phenyl, nitro-substituted phenyl, $C_1$–$C_4$-alkyl-substituted phenyl or α-2,4-dichlorophenoxyethyl, $R_6$ and $R_7$ can be identical or different and are hydrogen, $C_1$–$C_4$-alkyl, $C_1$–$C_3$-alkoxy-$C_1$–$C_4$-alkyl, dihalophenyl, cyclohexyl or methoxy, $R_8$, $R_9$ and $R_{10}$ can be identical or different and are methyl, ethyl, n-propyl or n-butyl, $R_{11}$ and $R_{12}$ can be identical or different and are methoxy, ethoxy, thiomethyl, thioethyl, thio-n-propyl, N,N-dimethylamino or N,N-diethylamino, $R_{13}$ is methyl, ethyl, phenyl or trifluoromethyl, $R_{14}$ and $R_{15}$ can be identical or different and are hydrogen, methyl, ethyl, n-propyl, iso-propyl, n-butyl, n-hexyl, n-heptyl, methoxy, ethoxy or isopropoxy, and m is 2 or 3, have an outstanding herbicidal action and are tolerated by a number of crops.

In formula I, $Z_1$, $Z_2$ and $Z_3$ can, independently of one another, each be, for example, hydrogen, fluorine, chlorine, bromine, iodine, nitro, cyano, carboxyl, methyl ethyl, n-propyl, iso-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy, tert.-butoxy, trichloromethoxy, trifluoromethoxy, 1-chloroethoxy, 2-chloroethoxy, 1-fluoroethoxy, 2-fluoroethoxy, 2,2,2-trichloroethoxy, 2,2,2-trifluoroethoxy, 1,1,2,2-tetrafluoroethoxy, 1,1,2,2,2-pentafluoroethoxy, methylmercapto, ethylmercapto, trichloromethylmercapto, trifluoromethylmercapto, methylsulfinyl, ethylsulfinyl, methylsulfonyl, ethylsulfonyl or trifluoromethylsulfonyl, the following arrangements of substituents being preferred:

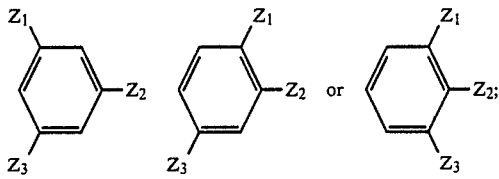

$Z_4$ can be, for example, hydrogen, cyano, methyl, ethyl, n-propyl, iso-propyl, n-butyl, iso-propyl, iso-butyl, tert.-butyl, methoxy, ethoxy, propoxy, butoxy, methylmercapto, ethylmercapto or propylmercapto, Y can be, for example, hydrogen, fluorine, chlorine, bromine, iodine, cyano or nitro, X can be, for example, oxygen, sulfur, sulfinyl or sulfonyl, and A can be, for example, hydrogen, methyl, ethyl, n-propyl, 2-propyl, n-butyl, 2-butyl, 3-butyl, 2,2-dimethylethyl, n-pentyl and any isomeric pentyl radical, n-hexyl and any isomeric hexyl radical and substituted

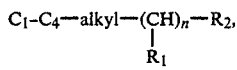

where $R^1$ is hydrogen, methyl, ethyl or n-propyl, $R_2$ is cyano, methoxy, ethoxy or

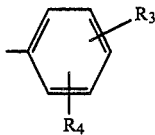

$$-\overset{O}{\underset{\|}{C}}B,$$

and B is OH, ONa, OCH$_3$, OC$_2$H$_5$, O—i—C$_3$H$_7$, O—(C$_4$–C$_{20}$)-alkyl, O-phenyl, substituted phenoxy, —NH$_2$, —NH—(C$_1$–C$_4$)-alkyl or —N(C$_1$–C$_4$-alkyl)$_2$, and n is 1, 2 or 3; A can also be tetrahydrofurfuryl, C$_1$–C$_4$-alkyl-substituted tetrahydrofurfuryl, phenyl, substituted phenyl

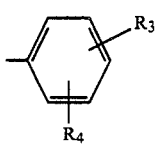

where $R_3$ and $R_4$ can be identical or different and are hydrogen, halogen (fluorine, chlorine or bromine), methyl, nitro, cyano, methoxy, carboxyl, trifluoromethyl or an O-propionic acid methyl ester group, benzyl, substituted benzyl

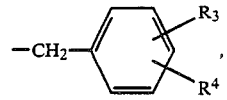

where $R_3$ and $R_4$ have the above meanings, acyl

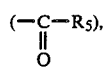

where $R_5$ is methyl, ethyl, propyl, chloromethyl, dichloromethyl, trichloromethyl, methoxymethyl, phenyl, C$_1$–C$_4$-alkyl-substituted phenyl or α-2,4-dichlorophenoxyethyl, carbamyl

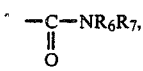

where $R_6$ and $R_7$ can be identical or different and are hydrogen, C$_1$–C$_4$-alkyl (methyl or ethyl), C$_1$–C$_3$-alkoxy-C$_1$–C$_4$-alkyl (methoxyethyl), dihalophenyl, cyclohexyl or methoxy, silyl

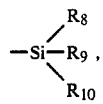

where $R_8$, $R_9$ and $R_{10}$ can be identical or different and are methyl, ethyl, n-propyl or n-butyl, and phosphatyl

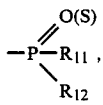

where $R_{11}$ and $R_{12}$ can be identical or different and are methoxy, ethoxy, thiomethyl, thioethyl, thio-n-propyl, N,N-dimethylamino or N,N-diethylamino; when X is oxygen, A can also be sulfonyl —SO$_2$R$_{13}$, where $R_{13}$ is methyl, ethyl, phenyl or trifluoromethyl, and sulfamyl —SO$_2$NR$_{14}$R$_{15}$, where $R_{14}$ and $R_{15}$ can be identical or different and are hydrogen, methyl, ethyl, n-propyl, iso-propyl, n-butyl, n-hexyl, n-heptyl, methoxy, ethoxy or isopropoxy; when $Z_4$ is alkoxy or alkylmercapto, A can also be a methylene chain —(CH$_2$)$_m$— by which the radicals $Z_4$—CH—X— are bonded to form a ring, m being 2 or 3.

Lower alkyl is alkyl of 1 to 4 carbon atoms.

The equations which follow represent examples of the preparation of the novel compounds of the formula I:

Equation (a)

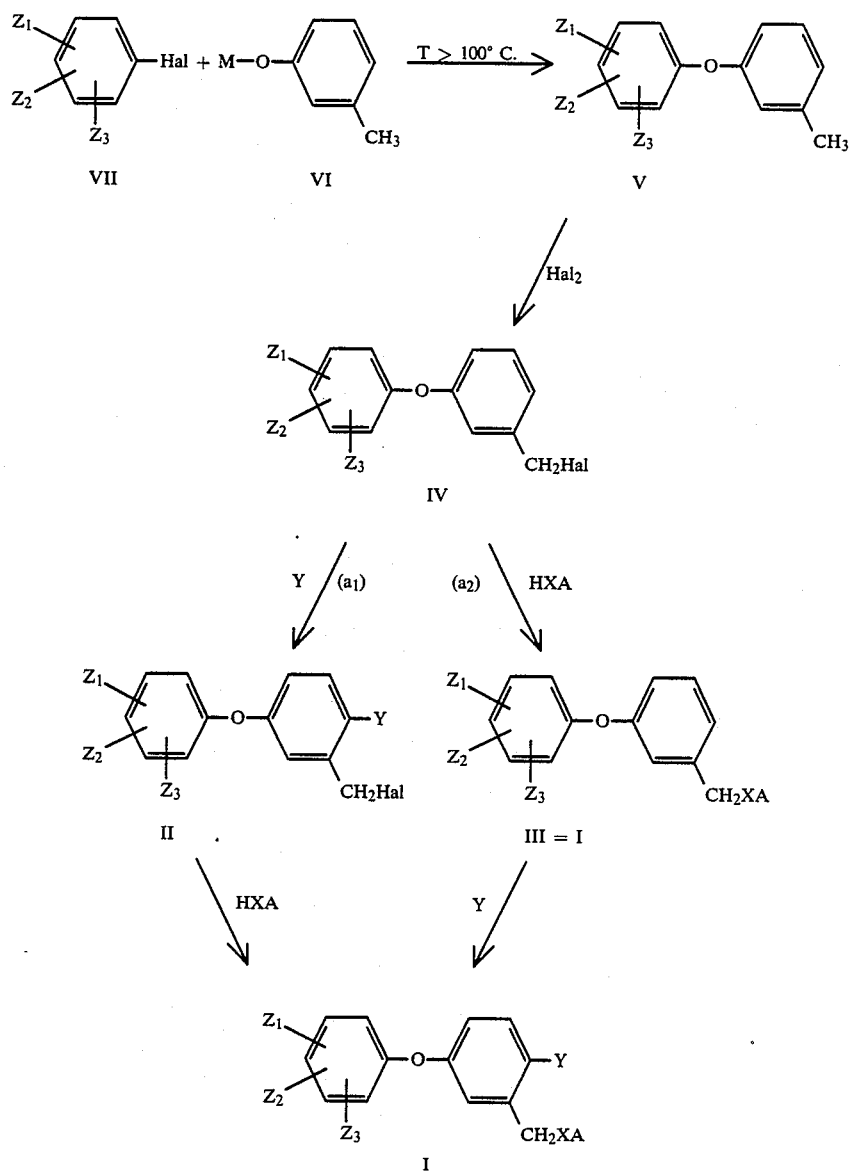

In these formulae, $Z_1$, $Z_2$, $Z_3$, X, Y and A have the meanings given under formula I, Hal is halogen, preferably chlorine or bromine, and M is a metal cation, preferably sodium or potassium. A substituted halobenzene of the general formula VII is condensed with the alkali metal salt of the meta-cresol of the general formula VI, in a polar aprotic solvent, for example dimethylsulfoxide, dimethylformamide or N-methylpyrrolidone, at from 80° C. to 200° C., and the corresponding 3-methyldiphenyl ether of the general formula V is obtained in good yields. The conversion of this compound into the halomethyl compound can be carried out very simply and economically by direct halogenation, with or without an inert solvent being present, a free radical initiator being added and the action of light being employed (Houben-Weyl, Volume 5/3, Georg Thieme Verlag, Stuttgart 1962, page 736; German Laid-Open Application DOS 2,844,270), or with the aid of halogenating agents, such as sulfuryl chloride or N-bromosuccinimide, in an inert solvent and with the addition of free radical initiators (Houben-Weyl, Volume 5/3, Georg Thieme Verlag, Stuttgart, 1962, page 892 and Volume 5/4, 1960, page 341).

The novel end products of the general formula I can be prepared, for example, via two routes.

In route (a₁), the particular substituent Y (differing from H) is first introduced by a conventional process such as nitration (nitric acid/sulfuric acid) or halogenation and the correspondingly substituted halomethyl compound of the general formula II is obtained in good yields. Further reaction with an alcohol or thiol HXA in the presence of an acid acceptor, or in the form of its alkali metal salt and in an inert solvent, gives the end product of the general formula I.

In route (a₂), the halomethyl compound IV is first reacted, as described in (a₁), with the alcohol or thiol to give the benzyl ether of the general formula III, which is at the same time identical to the end product where Y is H. By introducing the substituent Y, the end product of the general formula I is finally obtained, as indicated.

Equation (b)

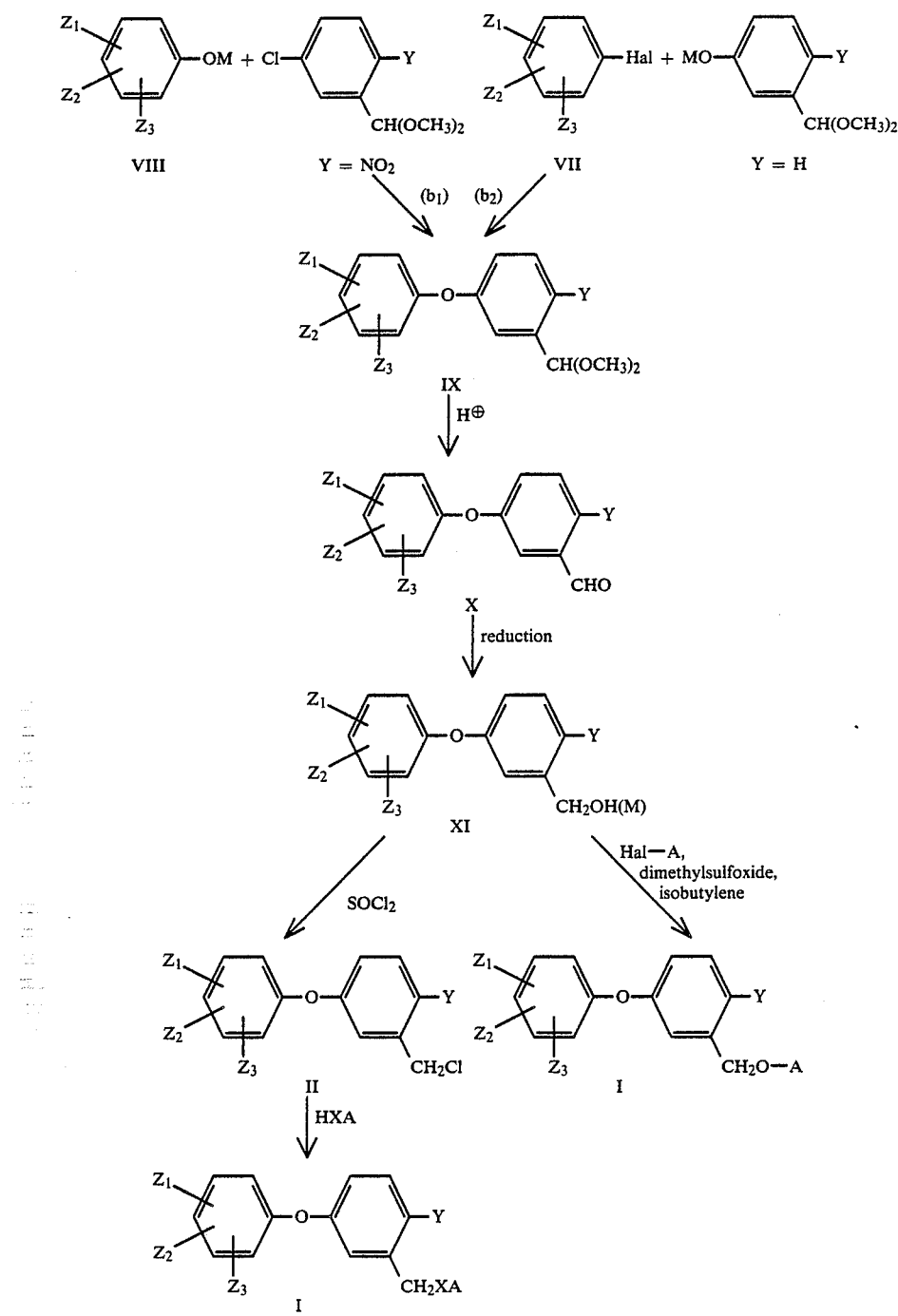

In these formulae, $Z_1$, $Z_2$, $Z_3$, X, Y and A have the meanings given under formula I, Hal is halogen, preferably chlorine or bromine, and M is a metal cation, preferably sodium or potassium.

The preparation of the benzyl alcohol of the general formula XI, the starting point for the synthesis of the desired end product of the general formula I, can be carried out via two possible routes. In process (b₁), the alkali metal salt of the appropriately substituted phenol is condensed with the 5-chloro-2-nitrobenzaldehyde-dimethylacetal (J. Amer. Chem. Soc. 74 (1952), 536) in a polar aprotic solvent, eg. dimethylsulfoxide, dimethylformamide or N-methylpyrrolidone, at from 80° to 200° C., and the corresponding diphenyl ether benzaldehyde-dimethylacetal of the general formula IX, where Y is $NO_2$, is obtained in good yield. In process (b₂), the reaction of the halobenzene of the general formula VII with the alkali metal salt of the 3-hydroxybenzaldehyde-dimethylacetal gives the diphenyl ether benzaldehyde-dimethylacetal IX, where Y is H, under the same reaction conditions as in (b₁). However, Y can be converted into nitro by nitration with nitric acid in glacial acetic acid at from 0° C. to 5° C., or into halogen by halogenation with elementary halogen in glacial acetic acid. The benzyl alcohol of the general formula XI can be obtained by acid hydrolysis of the acetal with concentrated mineral acid and subsequent reduction of the aldehyde X with a reducing agent, such as sodium borohydride or aluminum isopropylate, in an inert solvent. The end product of the general formula I can then be obtained by directly reacting the benzyl alcohol XI with an acylating or alkylating component by methods which are well known from the literature; it is also possible to react the benzyl alcohol in the form of its alkali metal salt. By means of thionyl chloride or other chlorinating agents, the benzyl alcohol XI can also be converted into the benzyl chloride II, from which the end product of the general formula I can be obtained by the method of equation (a).

The advantages of the above procedure for the preparation of the herbicidal diphenyl ethers of the general formula I are that cheaper, more readily obtainable starting materials can be employed (particularly in procedure (a) and that high yields are obtained in the individual reaction steps. Furthermore, owing to the variety of possible intermediates, a large number of end products of different biological properties can be synthesized.

The Examples which follow illustrate the preparation of the novel compounds of the general formula I according to the processes indicated. Parts by weight bear the same relation to parts by volume as that of the kilogram to the liter.

EXAMPLE 1

(a) 73 parts by weight of potassium 3-cresolate, 107 parts by weight of 3,4-dichlorobenzotrifluoride and 6.9 parts by weight of potassium carbonate in 500 parts by volume of dimethylsulfoxide were stirred at 140° C. for 8 hours. The reaction mixture was cooled to room temperature and was poured into 2,000 parts by volume of water. The oily residue was taken up in ether, and the organic phase was dried with magnesium sulfate, filtered, and concentrated under reduced pressure. Fractional distillation gave 120 parts by weight (84% of theory) of 3-(2'-chloro-4'-trifluoromethylphenoxy)-toluene of boiling point 91°–96° C./0.1 bar and refractive index $n_D^{25}$: 1.5268.

(b) 65 parts by weight of 3-(2'-chloro-4'-trifluoromethylphenoxy)-toluene and 2 parts by weight of phosphorus pentachloride were treated with chlorine gas for half an hour at 200° C. Fractional distillation gave 43.2 parts by weight (60% of theory) of 3-(2'-chloro-4'-trifluoromethylphenoxy)-benzyl chloride of boiling point 135°–145° C. and refractive index $n_D^{25}$: 1.5427.

(c) A solution of 5.3 parts by weight of methyl thioacetate in 20 parts by volume of absolute tetrahydrofuran was added, a little at a time, to a suspension of 1.5 parts by weight of 80% strength sodium hydride in 50 parts by volume of absolute tetrahydrofuran, at room temperature. The mixture was stirred at room temperature for a further half-hour and a solution of 16 parts by weight of 3-(2'-chloro-4'-trifluoromethylphenoxy)-benzyl chloride in 50 parts by volume of absolute tetrahydrofuran was then added dropwise. The reaction mixture was refluxed, stirred for a further 3 hours, cooled, and concentrated under reduced pressure. The oily residue was taken up in ether, the solution was extracted with water, the organic phase was dried with magnesium sulfate and the ether was stripped off under reduced pressure. 19.5 parts by weight (92% of theory) of methyl 3-(2'-chloro-4'-trifluoromethylphenoxy)-benzyl thioacetate (compound No. 1) of refractive index $n_D^{25}$: 1.5452 were obtained.

EXAMPLE 2

(a) 206 parts by weight of the potassium salt of 3-hydroxybenzaldehyde-dimethylacetal (prepared by concentrating to dryness a solution of 56 parts by weight of potassium hydroxide and 168 parts by weight of 3-hydroxybenzaldehyde-dimethylacetal in 500 parts by volume of absolute methanol), 50 parts by weight of potassium carbonate and 215 parts by weight of 3,4-dichlorobenzotrifluoride were suspended in 1,000 parts by volume of dimethylsulfoxide and the suspension was then stirred at 150° C. for 5 hours. The reaction mixture was cooled and stirred into 5,000 parts by volume of water, and the aqueous phase was then decanted from the oily phase which had separated out. The latter was taken up in ether, the solution was dried with magnesium sulfate and filtered, the ether was evaporated under reduced pressure and the residue was subjected to fractional distillation. 250 parts by weight (72% of theory) of 3-(2'-chloro-4'-trifluoromethylphenoxy)-benzaldehyde-dimethylacetal (compound No. 2) of boiling point 135°–145° C./1 bar and refractive index $n_D^{25}$: 1.5181 were obtained.

(b) 173 parts by weight of 3-(2'-chloro-4'-trifluoromethylphenoxy)-benzaldehyde-dimethylacetal were dissolved in 200 parts by volume of dioxane, and 88 parts by volume of concentrated sulfuric acid were added, a little at a time, to the solution. The mixture was stirred at 30° C. for half an hour and 2,000 parts by weight of ice were added. The oil which separated out was taken up in ether, and the ether phase was washed with dilute sodium bicarbonate solution and with water, dried with magnesium sulfate, filtered, and concentrated under reduced pressure. 148 parts by weight (99% of theory) of 3-(2'-chloro-4'-trifluoromethylphenoxy)-benzaldehyde of refractive index $n_D^{25}$: 1.5412 were obtained.

(c) A solution of 90 parts by weight of 3-(2'-chloro-4'-trifluoromethylphenoxy)-benzaldehyde in 300 parts by volume of ethylene glycol dimethyl ether was added dropwise to a suspension of 5.7 parts by weight of sodium borohydride in 200 parts by volume of ethylene glycol dimethyl ether at 0° C. The reaction mixture was further stirred for 12 hours at room temperature, 500 parts by volume of water were added and the mixture was acidified with 10% strength sulfuric acid. It was then extracted with ether, the organic phase was dried with magnesium sulfate and filtered, and the solvent was evaporated under reduced pressure. Fractional distillation of the residue gave 80 parts by weight (89% of theory) of 3-(2'-chloro-4'-trifluoromethylphenoxy)-benzyl alcohol (compound No. 3) of boiling point 140°–145° C./0.1 bar and refractive index $n_D^{25}$: 1.5330.

(d) 3.25 parts by weight of 80% strength sodium hydride were suspended in 100 parts by volume of absolute tetrahydrofuran and a solution of 30 parts by weight of 3-(2'-chloro-4'-trifluoromethylphenoxy)-benzyl alcohol in 50 parts by volume of absolute tetrahydrofuran was then added, a little at a time. The mixture was stirred at 40° C. for half an hour and a solution of 15 parts by weight of methyl bromoacetate in 50 parts by volume of absolute tetrahydrofuran was added. The reaction mixture was then stirred at the boil for 2 hours, and was cooled and concentrated under reduced pressure. The oily residue was taken up in ether, and the organic phase was extracted with water, dried with magnesium sulfate and evaporated down under reduced pressure. Fractional distillation of the residue gave 19 parts by weight (51% of theory) of methyl 3-(2'-chloro- 4'-trifluoromethylphenoxy)-benzoxyacetate (compound No. 4) of boiling point 150°–160° C./0.2 bar and refractive index $n_D^{25}$: 1.5268.

EXAMPLE 3

A solution of 19 parts by weight of methyl 3-(2'-chloro-4'-trifluoromethylphenoxy)-benzoxyacetate in 60 parts by volume of acetic anhydride was nitrated, at from 0° to 5° C., with a mixture of 6.2 parts by weight of 65% strength nitric acid and 6.2 parts by weight of concentrated sulfuric acid. Stirring was then continued at 5° C. for 2 hours, and the reaction mixture was stirred into 500 parts by volume of water and extracted with twice 200 parts by volume of methylene chloride. The organic phase was dried with magnesium sulfate, filtered and concentrated under reduced pressure. The oily residue was chromatographed over silica gel with acetone/toluene (30:70). 22 parts by weight (52% of theory) of methyl 3-(2'-chloro-4'-trifluoromethylphenoxy)-6-nitrobenzoxyacetate (compound No. 5) of refractive index $n_D^{25}$: 1.5472 were obtained.

EXAMPLE 4

A suspension of 202 parts by weight of potassium 2,4-dichlorophenolate, 231 parts by weight of 3-chloro-6-nitrobenzaldehyde-dimethylacetal and 50 parts by weight of potassium carbonate in 600 parts by volume of dimethylsulfoxide was stirred at 120° C. for 24 hours. After cooling, the reaction mixture was stirred into 5,000 parts by volume of water, the aqueous phase was decanted from the oil which had separated out, and the residue was taken up in ether. The organic phase was treated with dilute sodium hydroxide solution and three times with water, dried with magnesium sulfate and filtered, and the ether was evaporated under reduced pressure. 320 parts by weight (89% of theory) of 3-(2',4'-dichlorophenoxy)-6-nitrobenzaldehyde-dimethylacetal (compound No. 6) of refractive index $n_D^{25}$: 1.5712 were obtained.

EXAMPLE 5

(a) 156 parts by weight (82% of theory) of 3-(2',4'-dichlorophenoxy)-5-nitrobenzaldehyde of melting point 94°–96° C. (recrystallized from diisopropyl ether) were obtained from 179 parts by weight of 3-(2',4'-dichlorophenoxy)-6-nitro-benzaldehyde-dimethylacetal, similarly to Example (2b).

(b) A suspension of 62 parts by weight of 3-(2',4'-dichlorophenoxy)-6-nitrobenzaldehyde and 41 parts by weight of aluminum isopropylate in 300 parts by volume of absolute isopropanol was refluxed. The acetone formed during the reaction was continuously distilled off until the reaction had ended. The mixture was then stirred under reflux for a further half an hour, after which the isopropanol was distilled off under reduced pressure. 100 parts by weight of ice were added to the residue, and the mixture was hydrolyzed with 110 parts by volume of 6N sulfuric acid. The mixture was extracted with ether, the ether phase was washed once with water, dried with magnesium sulfate and filtered, the solvent was evaporated off under reduced pressure and the residue was recrystallized from ethanol. 57 parts by weight (92% of theory) of 3-(2',4'-dichlorophenoxy)-6-nitrobenzyl alcohol (compound No. 7) of melting point 115°–120° C. were obtained.

(c) A suspension was formed by vigorously stirring 15.7 parts by weight of 3-(2',4'-dichlorophenoxy)-6-nitrobenzyl alcohol, 0.1 part by weight of tetrabutylammonium bromide, 100 parts by volume of methylene chloride and 10 parts by weight of 50% strength sodium hydroxide solution. 7.55 parts by weight of dimethyl sulfate were added to this suspension at room temperature and stirring was continued for 3 hours. 300 parts by volume of water were then added to the reaction mixture, the organic phase was separated off, washed twice with water, dried with magnesium sulfate and filtered, and the solvent was evaporated off under reduced pressure. The oily residue was taken up on methylene chloride and chromatographed over neutral aluminum oxide. 8 parts by weight (49% of theory) of 3-(2',4'-dichlorophenoxy)-6-nitrobenzyl methyl ether (compound No. 8) of melting point 79°–83° C. were obtained.

EXAMPLE 6

A mixture of 124 parts by weight of 65% strength nitric acid and 128 parts by weight of concentrated sulfuric acid was added dropwise to a solution of 346 parts by weight of 3-(2'-chloro-4'-trifluoromethylphenoxy)benzaldehyde-dimethylacetal in 600 parts by volume of acetic anhydride at from 0° to 5° C. Stirring was continued at 5° C. for 2 hours and the reaction mixture was then introduced into 5,000 parts by weight of ice. The precipitate was filtered off under suction, dried, stirred with methyl tert.-butyl ether and again filtered off under suction. 380 parts by weight (85% of theory) of 3-(2'-chloro-4'-trifluoromethylphenoxy)-6-nitrobenzaldehydediacetate (compound No. 9) of melting point 108°–111° C. were obtained.

EXAMPLE 7

(a) 330 parts by weight (96% of theory) of 3-(2'-chloro-4'-trifluoromethylphenoxy)-6-nitrobenzaldehyde of melting point 94°–96° C. (recrystallized from diisopropyl ether) were obtained by acid hydrolysis of 447 parts by weight of 3-(2'-chloro-4'-trifluoromethylphenoxy)-6-nitrobenzaldehyde diacetate, similarly to Example (2b).

(b) 17.3 parts by weight of 3-(2'-chloro-4'-trifluoromethylphenoxy)-6-nitrobenzaldehyde and 4.7 parts by weight of ethanedithiol in 100 parts by volume of absolute toluene were stirred under reflux for 3 hours. The reaction mixture was concentrated under reduced pressure and 21 parts by weight (100% of theory) of 3-(2'-chloro-4'-trifluoromethylphenoxy)-6-nitrobenzaldehyde-1,3-dithiolane (compound No. 10) of melting point 68°–72° C. were obtained.

EXAMPLE 8

(a) 22 parts by weight (63% of theory) of 3-(2'-chloro-4'-trifluoromethylphenoxy)-6-nitrobenzyl alcohol (compound No. 11) of melting point 89°–92° C. (recrystallized from diisopropyl ether) were obtained by reducing 34.6 parts by weight of 3-(2'-chloro-4'-trifluoromethylphenoxy)-6-nitrobenzaldehyde with sodium borohydride, similarly to Example (2c).

(b) 7.8 parts by weight of isopropylamidosulfonyl chloride and 5.1 parts by weight of triethylamine were simultaneously added dropwise to a solution of 17.4 parts by weight of 3-(2'-chloro-4'-trifluoromethylphenoxy)-6-nitrobenzyl alcohol in 150 parts by volume of absolute tetrahydrofuran. The reaction mixture was then stirred further for 2 hours under reflux. After the mixture had cooled, the precipitate was filtered off under suction and the filtrate was concentrated under reduced pressure. The oily residue was stirred with 50 parts by volume of 1N sodium hydroxide solution, the solution was filtered and 2N hydrochloric acid was added until the pH is 2. The precipitate was filtered off under suction and dried, giving 18 parts by weight (90% of theory) of 3-(2'-chloro-4'-trifluoromethylphenoxy)-6-nitrobenzyloxy-N-isopropyl (amido) sulfonate (compound No. 12) of melting point 89°–91° C.

EXAMPLE 9

(a) 34.8 parts by weight of 3-(2'-chloro-4'-trifluoromethylphenoxy)-6-nitrobenzyl alcohol were suspended in 200 parts by volume of absolute toluene, 8 parts by weight of pyridine were added, and 13.1 parts by weight of thionyl chloride were added dropwise at 0° C. Thereafter the reaction mixture was stirred for a further 2 hours at 110° C., was cooled, and was extracted with 75 parts by volume of 3N hydrochloric acid and with five times 250 parts by volume of water. The organic phase was separated off, dried with magnesium sulfate and concentrated under reduced pressure. 32 parts by weight (88% of theory) of 3-(2'-chloro-4'-trifluoromethylphenoxy)-6-nitrobenzyl chloride were obtained in the form of an initially oily residue which crystallized when triturated with pentane, to give crystals of melting point 55°–60° C.

(b) 1.44 parts by weight of 80% strength sodium hydride were suspended in 25 parts by volume of absolute tetrahydrofuran, and a solution of 5.31 parts by weight of methylthioacetate in 50 parts by volume of absolute tetrahydrofuran was added a little at a time at room temperature. Stirring was continued for half an hour and a solution of 18.3 parts by weight of 3-(2'-chloro-4'-trifluoromethylphenoxy)-6-nitrobenzyl chloride in 50 parts by volume of absolute tetrahydrofuran was then added. The reaction mixture was then stirred under reflux for a further 3 hours, was cooled, and was concentrated under reduced pressure. The residue was taken up in ether, the solution was extracted with water, the organic phase was separated off, dried with magnesium sulfate and filtered, and the ether was evaporated. The oily residue crystallized when triturated and was recrystallized from diisopropyl ether. 16 parts by weight (73% of theory) of methyl 3-(2'-chloro-4'-trifluoromethylphenoxy)-6-nitrobenzylthioacetate (compound No. 13) of melting point 61°–63° C. were obtained.

EXAMPLE 10

A solution of 19.5 parts by weight of metachloroperbenzoic acid in 200 parts by volume of chloroform was added a little at a time to a solution of 17.4 parts by weight of methyl 3-(2'-chloro-4'-trifluoromethylphenoxy)-6-nitrobenzylthioacetate in 200 parts by volume of chloroform at −10° C. The reaction mixture was allowed to stand for 48 hours at 5° C. and the precipitate formed was filtered off under suction. The filtrate was extracted with dilute aqueous sodium bicarbonate solution and water, dried with magnesium sulfate, filtered, and evaporated down under reduced pressure. The residue was triturated with pentane and 12 parts by weight (64% of theory) of methyl 3-(2'-chloro-4'-trifluoromethylphenoxy)-6-nitrobenzylsulfoacetate (compound No. 14) of melting point 82°–83° C. were obtained.

EXAMPLE 11

16 parts by weight of methyl 3-(2'-chloro-4'-trifluoromethylphenoxy)-6-nitrobenzylthioacetate in a solution of 2.5 parts by weight of potassium hydroxide in 15 parts by volume of ethanol and 15 parts by volume of water were refluxed for 3 hours. The mixture was cooled, diluted with 100 parts by volume of water and acidified with 2N hydrochloric acid. The oily residue was taken up with methylene chloride, the solution was dried with magnesium sulfate and filtered, and the solvent was evaporated off under reduced pressure. The residue was chromatographed over silica gel with toluene/acetone (70:30). 13.4 parts by weight (86% of theory) of 3-(2'-chloro-4'-trifluoromethylphenoxy)-6-nitrobenzylthioacetic acid (compound No. 15) of refractive index $n_D^{25}$: 1.5821 were obtained.

EXAMPLE 12

Isobutylene gas was passed into a solution of 17.4 parts by weight of 3-(2'-chloro-4'-trifluoromethylphenoxy)-6-nitrobenzyl alcohol in 100 parts by volume of 1,2-dichloroethane and 0.5 parts by weight of sulfuric acid at 40° C. for two hours. The reaction mixture was then washed with dilute aqueous sodium bicarbonate solution and twice with water, and the organic phase was dried with magnesium sulfate, filtered and concentrated. 18 parts by weight (89% of theory) of 3-(2'-chloro-4'-trifluoromethylphenoxy)-6-nitrobenzyl tert.-butyl ether (compound No. 16) of melting point 75°–78° C. were obtained.

EXAMPLE 13

A solution of dimethylammonium O-ethyl S-propyldithiophosphate in 100 parts by volume of acetone was added to 18.3 parts by weight of 3-(2'-chloro-4'-trifluoromethylphenoxy)-6-nitrobenzyl chloride in 100 parts by volume of absolute acetone at room temperature. The reaction mixture was refluxed for 7 hours, was then cooled, and was evaporated to dryness under reduced pressure. The residue was taken up in toluene, the solution was extracted with dilute aqueous sodium bicarbonate solution and with water, and the organic phase was dried with magnesium sulfate and concentrated under reduced pressure. 14 parts by weight (52% of theory) of O-ethyl S-propyl S-[3-(2'-chloro-4'-trifluoromethylphenoxy)-6-nitrobenzyl]dithiophosphate (compound No. 17) of refractive index $n_D^{25}$: 1.5666 were obtained.

EXAMPLE 14

A suspension of 17.3 parts by weight of 3-(2'-chloro-4'-trifluoromethylphenoxy)-6-nitrobenzaldehyde, 22.5 parts by weight of a 40% strength sodium bisulfite solution and 63 parts by volume of water was first stirred for half an hour at 40° to 50° C. and then cooled to 0° C., and 200 parts by volume of ether, followed by a solution of 4.88 parts by weight of potassium cyanide in 63 parts by volume of water, were added to the suspension. After a pinch of triethylbenzylammonium chloride had been added to the mixture, stirring was continued, initially for 2 hours at room temperature and then for 2 hours under reflux. The mixture was cooled, the ether phase was separated off, washed with dilute aqueous sodium bicarbonate solution and water and dried with magnesium sulfate, and the solvent was stripped off under reduced pressure. 10 parts by weight (54% of theory) of 3-(2'-chloro-4'-trifluoromethylphenoxy)-6-nitro-α-cyanobenzyl alcohol (compound No. 18) of refractive index $n_D^{25}$: 1.5650 were obtained.

EXAMPLE 15

(a) 58.2 parts by weight of bromine were added dropwise to a solution of 32.1 parts by weight of 3-(2'-chloro-4'-trifluoromethylphenoxy)-benzyl chloride at 20° C., whilst stirring. The reaction mixture was further stirred under reflux for 8 hours, was cooled, and was concentrated to dryness under reduced pressure. The oily residue was taken up in methylene chloride, and the solution was washed three times with aqueous sodium bicarbonate solution and twice with water, dried with magnesium sulfate, filtered, and concentrated under reduced pressure. Fractional distillation gave 28 parts by weight (70% of theory) of 3-(2'-chloro-4'-trifluoromethylphenoxy)-6-bromobenzyl bromide of boiling point 148°–155° C./0.1 bar and refractive index $n_D^{25}$:1.5884.

(b) A solution of 7.9 parts by weight of 4-chlorobenzylmercaptan in 50 parts by volume of absolute tetrahydrofuran was added dropwise to a suspension of 1.5 parts by weight of 80% strength sodium hydride in 50 parts by volume of absolute tetrahydrofuran, and the mixture was stirred for half an hour at room temperature. A solution of 22.3 parts by weight of 3-(2'-chloro-4'-trifluoromethylphenoxy)-6-bromobenzyl bromide in 60 parts by weight of tetrahydrofuran was then added dropwise, the mixture was refluxed and stirring was continued for 2 hours. The reaction mixture was cooled, and concentrated under reduced pressure, and the oily residue was taken up in ether. The organic phase was washed once with water, dried with magnesium sulfate, filtered, and concentrated to dryness, giving 16 parts by weight (61% of theory) of 3-(2'-chloro-4'-trifluoromethylphenoxy)-6-bromobenzyl 4''-chlorobenzyl thioether (compound No. 19) of refractive index $n_D^{25}$: 1.5952.

The following compounds were obtained analogously:

| Compound no. | $Z_3$ = D | Y | $Z_4$ | X | A | m.p. [°C.]; $n_D^{25}$, Wavelength of a band in the infrared spectrum |
|---|---|---|---|---|---|---|
| 20 | 2'-Chloro-4'-trifluoromethylphenyl | H | H | O | $CH_3$ | 1.5187 |
| 23 | " | " | " | " | —$C(CH_3)_3$ | 42–45 |
| 28 | " | " | " | " | $CH_2$—(tetrahydrofuran-2-yl) | 1.5258 |
| 43 | " | " | H | " | CHCOOCH$_3$ \| CH$_3$ | 1.5105 |
| 57 | " | " | " | " | (phenyl)—O—CH(CH$_3$)—COCH$_3$ | 1.5462 |
| 67 | " | " | " | " | CO—(2-nitrophenyl) | 1.5641 |
| 74 | " | " | " | " | $CONHCH_3$ | 82–87 |
| 84 | " | " | " | " | $P(O)(OC_2H_5)(N(CH_3)_2)$ | 1.5399 |
| 85 | " | " | O | O | —$(CH_2)_2$— | 52–55 |
| 87 | " | " | $NO_2$ | H | O | $CH_3$ | 80–85 |
| 94 | " | " | " | " | $SO_2$ | $CH_3$ | 110–113 |
| 96 | " | " | " | " | S | $CH_2CH_2CN$ | C—N = 2240 |
| 101 | " | " | " | " | S | 4-Chlorobenzyl | 1.6142 |
| 104 | " | " | " | " | O | $CH_2$—(tetrahydrofuran-2-yl) | 1.5360 |
| 105 | " | " | Br | " | " | $CH_2$—(tetrahydrofuran-2-yl) | 1.5446 |

-continued

| Compound no. | $Z_1, Z_2, Z_3 = D$ (phenyl) | Y | $Z_4$ | X | A | m.p. [°C.]; $n_D^{25}$, Wavelength of a band in the infrared spectrum |
|---|---|---|---|---|---|---|
| 120 | " | $NO_2$ | H | O | $CH(CH_3)-COOCH_3$ | 1.5345 |
| 140 | " | " | " | S | $CH(CH_3)-COOCH_3$ | 1.5541 |
| 142 | " | " | " | " | $CH(CH_3)-COOH$ | 1.5636 |
| 145 | " | " | " | " | $CH_2CH_2COOC_{12}H_{25}$ | 1.5188 |
| 148 | " | " | " | S=O | $CH_2COOCH_3$ | 98–100 |
| 149 | " | " | " | " | $CH_2COOH$ | 144–146 |
| 152 | " | " | " | $SO_2$ | $CH_2COOCH_3$ | 80–81 |
| 153 | " | " | " | " | $CH_2COOH$ | 95–97 |
| 156 | " | " | Br | " | S | $CH_2COOCH_3$ | 1.5691 |
| 164 | " | " | " | " | $CH_2COOC_{18}H_{37}$ | C=o 1730 |
| 166 | " | " | " | " | $CH_2CH_2COOC_{12}H_{25}$ | 1.5138 |
| 167 | " | " | " | " | $CH_2CH_2COOC_{18}H_{37}$ | C=o 1720 |
| 173 | " | $NO_2$ | " | O | 4-F—phenyl | $NO_2$ = 1560 |
| 175 | " | " | " | " | phenyl-O-CH(CH_3)-COCH_3 | 1.5654 |
| 178 | " | " | " | " | S | 2,4-Dichlorophenyl | 1.6052 |
| 179 | " | " | " | " | S | 4-$OCH_3$—phenyl | 1.5980 |
| 180 | " | " | " | " | " | 2-Carboxyphenyl | 157–161 |
| 183 | " | " | Br | " | S | 4-Methoxyphenyl | 1.5958 |
| 186 | " | " | $NO_2$ | " | O | $COCH_3$ | 1.5454 |
| 189 | " | " | " | " | S | $COCH(CH_3)-O-(2,4-dichlorophenyl)$ | 1.5669 |
| 199 | " | " | " | " | " | $CNH-(3-Cl,4-F-phenyl)$, C=O | 140–142 |
| 203 | " | " | " | " | " | $Si(CH_3)_3$ | 58–62 |
| 210 | " | " | " | " | " | $P(=S)(OCH_3)_2$ | P=S = 830 |
| 212 | " | " | " | " | " | $P(=O)(OC_2H_5)(N(CH_3)_2)$ | P=O = 1260 |
| 213 | " | " | Br | H | S | $P(=S)(N-i-propyl)(OC_2H_5)$ | 1.5444 |
| 214 | " | " | $NO_2$ | O | O | $-(CH_2)_2-$ | 1.5541 |
| 216 | 2',4'-Dichlorophenyl | " | " | H | O | $C_2H_5$ | 60–63 |
| 230 | " | " | " | " | S | $CH_2COOCH_3$ | 1.6072 |
| 241 | " | " | " | " | O | $COCH_3$ | 70–75 |
| 242 | " | " | " | " | " | $COCH_2Cl$ | 1.6032 |
| 243 | " | " | " | " | " | $COCHCl_2$ | 1.5930 |
| 244 | " | " | " | " | " | $COCCl_3$ | 1.5958 |

| Compound no. | $Z_3$ ⟨$Z_1$, $Z_2$⟩ = D | Y | $Z_4$ | X | A | m.p. [°C]; $n_D^{25}$, Wavelength of a band in the infrared spectrum |
|---|---|---|---|---|---|---|
| 245 | " | " | " | " | $COCH_2OCH_3$ | 70–74 |
| 246 | " | " | " | " | $COCCl_2CH_3$ | 75–77 |
| 247 | " | " | " | " | CO—C₆H₅ | 142–146 |
| 248 | " | " | " | " | CO—CH(CH₃)—O—(2,4-dichlorophenyl) | 94–99 |
| 249 | " | " | " | " | $SO_2CH_3$ | 92–96 |
| 250 | " | " | " | " | $SO_2NHCH_3$ | 119–123 |
| 251 | " | " | " | " | $SO_2NH$—(i-propyl) | 88–92 |
| 253 | " | " | " | " | $\underset{\underset{O}{\|}}{C}NHCH_3$ | 135–140 |
| 258 | " | " | O | " | $(CH_2)_2$ | 1.5973 |
| 259 | 2',4'-Dibromophenyl | " | H | " | $CH_3$ | 87–93 |
| 260 | " | " | " | S | $CH_2CH_2CN$ | CN = 2240 |
| 261 | " | " | " | " | 4-Chlorobenzyl | $NO_2$ = 1340 |
| 263 | " | " | " | S | $CH_2COOCH_3$ | 1.6217 |
| 267 | " | " | " | SO | $CH_2COOCH_3$ | S=O = 1050 |
| 268 | " | " | " | $SO_2$ | $CH_2COOCH_3$ | $SO_2$ = 1340 |
| 269 | " | " | " | S | 4-Methoxyphenyl | 1.6528 |
| 272 | " | " | $OCH_3$ | O | $CH_3$ | 1.5810 |
| 273 | 2'-Chloro-4'-methyl-phenyl | " | H | " | H | 60–63 |
| 275 | " | " | " | S | $CH_2COOCH_3$ | 1.6041 |
| 277 | " | " | $OCH_3$ | O | $CH_3$ | 1.5727 |
| 278 | 2'-Bromo-4'-chlorophenyl | " | H | " | H | 90–93 |
| 280 | " | " | " | S | $CH_2COOCH_3$ | 1.630 |
| 281 | " | " | $OCH_3$ | O | $CH_3$ | 1.5753 |
| 282 | 2'-Chloro-4'-methoxyphenyl | " | H | " | H | 70–76 |
| 284 | " | " | " | S | $CH_2COOCH_3$ | 1.594 |
| 285 | " | " | $OCH_3$ | O | $CH_3$ | 1.5768 |
| 287 | " | " | $OCH_3$ | O | $CH_3$ | 1.5805 |
| 289 | 2'-Chloro-4'-fluorophenyl | " | " | " | $CH_3$ | 1.5555 |
| 291 | 4'-Fluorophenyl | " | " | " | $CH_3$ | 1.5568 |
| 292 | 2,6-Dibromo-4'-methylphenyl | " | H | S | $CH_2COOCH_3$ | 1.5981 |
| 293 | " | " | $OCH_3$ | O | $CH_3$ | 1.5579 |
| 294 | 2'-Chloro-4',5'-dimethylphenyl | " | H | " | H | 91–96 |
| 295 | " | " | " | S | $CH_2COOCH_3$ | 1.5999 |
| 296 | " | " | $OCH_3$ | O | $CH_3$ | 1.5762 |
| 299 | 2'-Chloro-4'-trifluoromethoxyphenyl | " | H | " | H | 88–94 |
| 301 | " | " | " | S | $CH_2COOCH_3$ | 1.5583 |
| 304 | " | " | $OCH_3$ | O | $CH_3$ | 1.5305 |
| 321 | 2'-Chloro-4'-trifluoromethylphenyl | " | H | S | $CH_2COO$—CH(CH₃)₂ | 66–68 |
| 322 | " | " | " | " | $CH_2COONa$ | C=O = 1600 |
| 323 | " | " | " | " | CH(CH₃)—COOH | 1.5636 |
| 324 | " | " | " | " | $CH_2COOC_2H_5$ | 58–61 |
| 325 | " | " | " | " | $CH_2CH_2COOC_{12}H_{25}$ | 1.5188 |
| 326 | " | " | " | " | $CH_2COOC_{18}H_{37}$ | C=O = 1720 |
| 327 | " | Br | " | " | $CH_2CH_2CN$ | 1.5738 |
| 328 | 2'-Nitro-4'-trifluoromethylphenyl | H | $OCH_3$ | O | $CH_3$ | 1.5225 |
| 329 | " | " | H | " | H | 1.5557 |
| 330 | 2'-Chloro-4'-trifluoromethylphenyl | Br | " | " | 4-Chlorophenyl | 1.5782 |

-continued

| Compound no. | Z₁ Z₂ Z₃ = D | Y | Z₄ | X | A | m.p. [°C.]; $n_D^{25}$, Wavelength of a band in the infrared spectrum |
|---|---|---|---|---|---|---|
| 331 | " | NO₂ | H | S | $\underset{\underset{O}{\|\|}}{C}NHCH_2CH_2OCH_3$ | 1.5778 |
| 332 | " | " | " | " | $\underset{\underset{O}{\|\|}}{C}N(CH_2CH_2OCH_3)_2$ | 1.5578 |
| 333 | " | " | " | " | $N(C_3H_7-i-)_2$ | 1.5508 |
| 334 | " | " | " | " | $\underset{C_3H_7(i)}{\overset{C_6H_{12}}{N}}$ | 1.5789 |

The following compounds may be obtained analogously:

| Compound no. | Z₁ Z₂ Z₃ = D | Y | Z₄ | X | A |
|---|---|---|---|---|---|
| 21 | 2'-Chloro-4'-trifluoromethylphenyl | H | H | O | $C_2H_5$ |
| 22 | 2'-Chloro-4'-trifluoromethylphenyl | " | " | " | $C_3H_7(n)$ |
| 24 | 2'-Chloro-4'-trifluoromethylphenyl | " | CN | " | $CH_3$ |
| 25 | 2'-Chloro-4'-trifluoromethylphenyl | " | " | " | $-C(CH_3)_3$ |
| 26 | 2'-Chloro-4'-trifluoromethylphenyl | " | H | " | Benzyl |
| 27 | 2'-Chloro-4'-trifluoromethylphenyl | " | " | " | 4-Chlorobenzyl |
| 29 | 2'-Chloro-4'-trifluoromethylphenyl | " | CN | " | $CH_2\text{-tetrahydrofuran-2-yl}$ |
| 30 | 2'-Chloro-4'-trifluoromethylphenyl | " | H | S | H |
| 31 | 2'-Chloro-4'-trifluoromethylphenyl | " | " | " | $CH_3$ |
| 32 | 2'-Chloro-4'-trifluoromethylphenyl | " | " | " | $C_2H_5$ |
| 33 | 2'-Chloro-4'-trifluoromethylphenyl | " | " | " | Benzyl |
| 34 | 2'-Chloro-4'-trifluoromethylphenyl | " | " | " | $CH_2\text{-tetrahydrofuran-2-yl}$ |
| 35 | 2'-Chloro-4'-trifluoromethylphenyl | " | " | SO | $CH_3$ |
| 36 | 2'-Chloro-4'-trifluoromethylphenyl | " | " | SO₂ | $CH_3$ |
| 37 | 2'-Chloro-4'-trifluoromethylphenyl | " | " | O | $CH_2COOC_2H_5$ |
| 38 | 2'-Chloro-4'-trifluoromethylphenyl | " | " | " | $CH_2COOC_{18}H_{37}$ |
| 39 | 2'-Chloro-4'-trifluoromethylphenyl | " | " | " | $CH_2COOH$ |
| 40 | 2'-Chloro-4'-trifluoromethylphenyl | " | " | " | $CH_2COONa$ |
| 41 | 2'-Chloro-4'-trifluoromethylphenyl | " | " | " | $CH_2CONHCH_3$ |
| 42 | 2'-Chloro-4'-trifluoromethylphenyl | " | CN | " | $CH_2COOCH_3$ |
| 44 | 2'-Chloro-4'-trifluoromethylphenyl | " | " | " | $\underset{CH_3}{\overset{\|}{CH}}COOCH_3$ |
| 45 | 2'-Chloro-4'-trifluoromethylphenyl | " | H | S | $CH_2COOC_2H_5$ |
| 46 | 2'-Chloro-4'-trifluoromethylphenyl | " | " | " | $CH_2COOC_3H_7(i)$ |
| 47 | 2'-Chloro-4'-trifluoromethylphenyl | " | " | " | $CH_2COONa$ |
| 48 | 2'-Chloro-4'-trifluoromethylphenyl | " | " | " | $CH_2COOC_{18}H_{37}$ |
| 49 | 2'-Chloro-4'-trifluoromethylphenyl | " | " | " | $CH_2CH_2COOCH_3$ |
| 50 | 2'-Chloro-4'-trifluoromethylphenyl | " | " | " | $CH_2CH_2COOC_{12}H_{25}$ |
| 51 | 2'-Chloro-4'-trifluoromethylphenyl | " | " | " | $CH_2CH_2COOC_{18}H_{37}$ |
| 52 | 2'-Chloro-4'-trifluoromethylphenyl | " | " | SO | $CH_2COOCH_3$ |
| 53 | 2'-Chloro-4'-trifluoromethylphenyl | " | " | SO₂ | $CH_2COOCH_3$ |
| 54 | 2'-Chloro-4'-trifluoromethylphenyl | H | H | " | $CH_2CH_2COOC_{12}H_{25}$ |
| 55 | 2'-Chloro-4'-trifluoromethylphenyl | " | " | O | Phenyl |
| 56 | 2'-Chloro-4'-trifluoromethylphenyl | " | " | " | 4-Chlorophenyl |

-continued

|   | Z₁  Z₂ (on phenyl ring) |   |   |   |   |
|---|---|---|---|---|---|

| Compound no. | Z₃ =D | Y | Z₄ | X | A |
|---|---|---|---|---|---|
| 58 | 2'-Chloro-4'-trifluoromethylphenyl | " | " | " | 3-CF₃—Phenyl |
| 59 | 2'-Chloro-4'-trifluoromethylphenyl | " | " | " | 2,4-Dichlorophenyl |
| 60 | 2'-Chloro-4'-trifluoromethylphenyl | " | " | S | Phenyl |
| 61 | 2'-Chloro-4'-trifluoromethylphenyl | " | " | " | 4-Chlorophenyl |
| 62 | 2'-Chloro-4'-trifluoromethylphenyl | " | " | " | 2,4-Dichlorophenyl |
| 63 | 2'-Chloro-4'-trifluoromethylphenyl | " | " | " | 4-Methoxyphenyl |
| 64 | 2'-Chloro-4'-trifluoromethylphenyl | " | " | O | COCH₃ |
| 65 | 2'-Chloro-4'-trifluoromethylphenyl | " | " | " | COCH₂Cl |
| 66 | 2'-Chloro-4'-trifluoromethylphenyl | " | " | " | CO—Phenyl |
| 68 | 2'-Chloro-4'-trifluoromethylphenyl | " | " | " | CO—C₆H₄—NO₂ (4-nitro) |
| 69 | 2'-Chloro-4'-trifluoromethylphenyl | " | " | " | SO₂CH₃ |
| 70 | 2'-Chloro-4'-trifluoromethylphenyl | " | " | " | SO₂CF₃ |
| 71 | 2'-Chloro-4'-trifluoromethylphenyl | " | " | " | SO₂NHCH₃ |
| 72 | 2'-Chloro-4'-trifluoromethylphenyl | " | " | " | SO₂NH—(i-propyl) |
| 73 | 2'-Chloro-4'-trifluoromethylphenyl | " | " | " | SO₂N(CH₃)₂ |
| 75 | 2'-Chloro-4'-trifluoromethylphenyl | " | " | " | CON(CH₃)₂ |
| 76 | 2'-Chloro-4'-trifluoromethylphenyl | " | " | " | CON(C₂H₅)₂ |
| 77 | 2'-Chloro-4'-trifluoromethylphenyl | " | " | " | CON(CH₃)(OCH₃) |
| 78 | 2'-Chloro-4'-trifluoromethylphenyl | " | " | S | CONHCH₃ |
| 79 | 2'-Chloro-4'-trifluoromethylphenyl | " | " | O | Si(CH₃)₃ |
| 80 | 2'-Chloro-4'-trifluoromethylphenyl | " | " | " | Si(C₂H₅)₃ |
| 81 | 2'-Chloro-4'-trifluoromethylphenyl | " | " | " | Si(CH₃)₂C₄H₉(n) |
| 82 | 2'-Chloro-4'-trifluoromethylphenyl | " | " | " | PO(OC₂H₅)₂ |
| 83 | 2'-Chloro-4'-trifluoromethylphenyl | " | " | " | PS(OC₂H₅)₂ |
| 86 | 2'-Chloro-4'-trifluoromethylphenyl | " | S | S | —(CH₂)₂— |
| 88 | 2'-Chloro-4'-trifluoromethylphenyl | NO₂ | CN | O | CH₃ |
| 89 | 2'-Chloro-4'-trifluoromethylphenyl | Br | H | " | CH₃ |
| 90 | 2'-Chloro-4'-trifluoromethylphenyl | Cl | " | " | CH₃ |
| 91 | 2'-Chloro-4'-trifluoromethylphenyl | CN | " | " | CH₃ |
| 92 | 2'-Chloro-4'-trifluoromethylphenyl | NO₂ | " | S | CH₃ |
| 93 | 2'-Chloro-4'-trifluoromethylphenyl | " | " | S=O | CH₃ |
| 95 | 2'-Chloro-4'-trifluoromethylphenyl | " | " | O | C₂H₅ |
| 97 | 2'-Chloro-4'-trifluoromethylphenyl | " | " | S | Benzyl |
| 98 | 2'-Chloro-4'-trifluoromethylphenyl | " | " | S=O | Benzyl |
| 99 | 2'-Chloro-4'-trifluoromethylphenyl | " | " | SO₂ | Benzyl |
| 100 | 2'-Chloro-4'-trifluoromethylphenyl | " | " | O | 4-Chlorobenzyl |
| 102 | 2'-Chloro-4'-trifluoromethylphenyl | Cl | " | S | 4-Chlorobenzyl |
| 103 | 2'-Chloro-4'-trifluoromethylphenyl | CN | " | " | 4-Chlorobenzyl |
| 106 | 2'-Chloro-4'-trifluoromethylphenyl | Cl | " | O | CH₂-(tetrahydrofuran-2-yl) |
| 107 | 2'-Chloro-4'-trifluoromethylphenyl | CN | " | " | CH₂-(tetrahydrofuran-2-yl) |
| 108 | 2'-Chloro-4'-trifluoromethylphenyl | NO₂ | " | S | H |
| 109 | 2'-Chloro-4'-trifluoromethylphenyl | " | " | O | CH₂COOC₂H₅ |
| 110 | 2'-Chloro-4'-trifluoromethylphenyl | " | " | " | CH₂COOH |
| 111 | 2'-Chloro-4'-trifluoromethylphenyl | " | " | " | CH₂COOC₁₈H₃₇ |
| 112 | 2'-Chloro-4'-trifluoromethylphenyl | " | " | " | CH₂COONa |

-continued

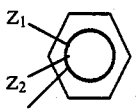

| Compound no. | $Z_3 = D$ | Y | $Z_4$ | X | A |
|---|---|---|---|---|---|
| 113 | 2'-Chloro-4'-trifluoromethylphenyl | " | " | " | $CH_2COO-C_3H_7(i)$ |
| 114 | 2'-Chloro-4'-trifluoromethylphenyl | " | " | " | $CH_2COO$—phenyl |
| 115 | 2'-Chloro-4'-trifluoromethylphenyl | " | " | " | $CH_2COO$—3-F—phenyl |
| 116 | 2'-Chloro-4'-trifluoromethylphenyl | " | " | " | $CH_2CONHCH_3$ |
| 117 | 2'-Chloro-4'-trifluoromethylphenyl | Br | " | " | $CH_2COOCH_3$ |
| 118 | 2'-Chloro-4'-trifluoromethylphenyl | Cl | " | " | $CH_2COOCH_3$ |
| 119 | 2'-Chloro-4'-trifluoromethylphenyl | CN | " | " | $CH_2COOCH_3$ |
| 121 | 2'-Chloro-4'-trifluoromethylphenyl | $NO_2$ | " | " | $\underset{CH_3}{CH}-COOH$ |
| 122 | 2'-Chloro-4'-trifluoromethylphenyl | " | " | " | $\underset{CH_3}{CH}-COO-Na$ |
| 123 | 2'-Chloro-4'-trifluoromethylphenyl | " | " | " | $\underset{CH_3}{CH}-CONHCH_3$ |
| 124 | 2'-Chloro-4'-trifluoromethylphenyl | " | " | S | $-CH_2\overset{O}{\overset{\|}{C}}O-\text{phenyl}$ |
| 125 | 2'-Chloro-4'-trifluoromethylphenyl | " | " | " | $-\underset{CH_3}{CH}-\overset{O}{\overset{\|}{C}}-O-\text{phenyl}$ |
| 126 | 2'-Chloro-4'-trifluoromethylphenyl | " | " | " | $-CH_2-\overset{O}{\overset{\|}{C}}NHCH_3$ |
| 127 | 2'-Chloro-4'-trifluoromethylphenyl | " | " | " | $-CH_2-\overset{O}{\overset{\|}{C}}-N(CH_3)_2$ |
| 128 | 2'-Chloro-4'-trifluoromethylphenyl | " | " | " | $-\underset{CH_3}{CH}-\overset{O}{\overset{\|}{C}}-NHC_2H_5$ |
| 129 | 2'-Chloro-4'-trifluoromethylphenyl | " | " | " | $-\underset{CH_3}{CH}-\overset{O}{\overset{\|}{C}}N(CH_3)_2$ |
| 130 | 2'-Chloro-4'-trifluoromethylphenyl | " | " | " | $-CH_2-\overset{O}{\overset{\|}{C}}O^\ominus NH_4^\oplus$ |
| 131 | 2'-Chloro-4'-trifluoromethylphenyl | " | " | " | $-\underset{C_2H_5}{CH}-\overset{O}{\overset{\|}{C}}OH$ |
| 132 | 2'-Chloro-4'-trifluoromethylphenyl | " | " | " | $-\underset{C_2H_5}{CH}-\overset{O}{\overset{\|}{C}}OCH_3$ |
| 133 | 2'-Chloro-4'-trifluoromethylphenyl | " | " | " | $-\underset{C_2H_5}{CH}-\overset{O}{\overset{\|}{C}}OC_2H_5$ |

-continued

| Compound no. | $Z_3 = D$ | Y | $Z_4$ | X | A |
|---|---|---|---|---|---|
| 134 | 2'-Chloro-4'-trifluoromethylphenyl | " | " | " | $-\underset{\underset{C_2H_5}{\mid}}{CH}-\overset{O}{\underset{\|}{C}}OC_{12}H_{25}$ |
| 135 | 2'-Chloro-4'-trifluoromethylphenyl | " | " | " | $-\underset{\underset{C_2H_5}{\mid}}{CH}-\overset{O}{\underset{\|}{C}}OC_{18}H_{37}$ |
| 136 | 2'-Chloro-4'-trifluoromethylphenyl | " | " | " | $-CH_2CH_2CH_2\overset{O}{\underset{\|}{C}}OH$ |
| 137 | 2'-Chloro-4'-trifluoromethylphenyl | " | " | " | $-CH_2CH_2CH_2\overset{O}{\underset{\|}{C}}OCH_3$ |
| 138 | 2'-Chloro-4'-trifluoromethylphenyl | " | " | " | $-CH_2CH_2CH_2\overset{O}{\underset{\|}{C}}OC_2H_5$ |
| 139 | 2'-Chloro-4'-trifluoromethylphenyl | " | " | " | $-CH_2CH_2CH_2\overset{O}{\underset{\|}{C}}NHCH_3$ |
| 141 | 2'-Chloro-4'-trifluoromethylphenyl | " | " | " | $\underset{\underset{CH-COOC_{12}H_{25}}{\mid}}{CH_3}$ |
| 143 | 2'-Chloro-4'-trifluoromethylphenyl | " | " | " | $\underset{\underset{CH-CONHCH_3}{\mid}}{CH_3}$ |
| 144 | 2'-Chloro-4'-trifluoromethylphenyl | " | " | " | $CH_2CH_2COOCH_3$ |
| 146 | 2'-Chloro-4'-trifluoromethylphenyl | " | " | " | $CH_2CH_2COOC_{18}H_{37}$ |
| 147 | 2'-Chloro-4'-trifluoromethylphenyl | " | " | " | $CH_2CH_2COOH$ |
| 150 | 2'-Chloro-4'-trifluoromethylphenyl | " | " | S=O | $\underset{\underset{CH_3}{\mid}}{CH}-COOCH_3$ |
| 151 | 2'-Chloro-4'-trifluoromethylphenyl | " | " | " | $\underset{\underset{CH_3}{\mid}}{CH}-COOH$ |
| 154 | 2'-Chloro-4'-trifluoromethylphenyl | " | " | $SO_2$ | $\underset{\underset{CH_3}{\mid}}{CH}-COOCH_3$ |
| 155 | 2'-Chloro-4'-trifluoromethylphenyl | " | " | " | $\underset{\underset{CH_3}{\mid}}{CH}-COOH$ |
| 157 | 2'-Chloro-4'-trifluoromethylphenyl | Cl | " | S | $CH_2COOCH_3$ |
| 158 | 2'-Chloro-4'-trifluoromethylphenyl | CN | " | S | $CH_2COOCH_3$ |
| 159 | 2'-Chloro-4'-trifluoromethylphenyl | Br | " | " | $\underset{\underset{CH_3}{\mid}}{CH}-COOCH_3$ |
| 160 | 2'-Chloro-4'-trifluoromethylphenyl | CN | " | " | $\underset{\underset{CH_3}{\mid}}{CH}-COOCH_3$ |
| 161 | 2'-Chloro-4'-trifluoromethylphenyl | Br | " | " | $CH_2-COOH$ |
| 162 | 2'-Chloro-4'-trifluoromethylphenyl | Br | H | S | $\underset{\underset{CH_3}{\mid}}{CH}-COOH$ |
| 163 | 2'-Chloro-4'-trifluoromethylphenyl | " | " | " | $CH_2-COOC_{12}H_{25}$ |
| 165 | 2'-Chloro-4'-trifluoromethylphenyl | " | " | " | $CH_2CH_2COOCH_3$ |

-continued

|  | Z₁⟨ring⟩ Z₂ Z₃ | | | | |
|---|---|---|---|---|---|
| Compound no. | Z₃ =D | Y | Z₄ | X | A |
| 168 | 2'-Chloro-4'-trifluoromethylphenyl | " | " | S=O | CH₂COOCH₃ |
| 169 | 2'-Chloro-4'-trifluoromethylphenyl | " | " | SO₂ | CH₂COOCH₃ |
| 170 | 2'-Chloro-4'-trifluoromethylphenyl | " | " | S=O | CH—COOCH₃<br>\|<br>CH₃ |
| 171 | 2'-Chloro-4'-trifluoromethylphenyl | " | " | SO₂ | CH—COOCH₃<br>\|<br>CH₃ |
| 172 | 2'-Chloro-4'-trifluoromethylphenyl | NO₂ | " | O | Phenyl |
| 174 | 2'-Chloro-4'-trifluoromethylphenyl | " | " | " | 3-CF₃—phenyl |
| 176 | 2'-Chloro-4'-trifluoromethylphenyl | " | " | " | 2,4-Dichlorphenyl |
| 177 | 2'-Chloro-4'-trifluoromethylphenyl | " | " | S | Phenyl |
| 181 | 2'-Chloro-4'-trifluoromethylphenyl | " | " | S=O | 2,4-Dichlorophenyl |
| 182 | 2'-Chloro-4'-trifluoromethylphenyl | " | " | SO₂ | 2,4-Dichlorophenyl |
| 184 | 2'-Chloro-4'-trifluoromethylphenyl | CN | " | S | 2,4-Dichlorophenyl |
| 185 | 2'-Chloro-4'-trifluoromethylphenyl | " | " | SO₂ | 2,4-Dichlorophenyl |
| 187 | 2'-Chloro-4'-trifluoromethylphenyl | NO₂ | " | O | COCH₂Cl |
| 188 | 2'-Chloro-4'-trifluoromethylphenyl | " | " | " | COCH₂OCH₃ |
| 190 | | " | " | O | CO—phenyl |
| 191 | 2'-Chloro-4'-trifluoromethylphenyl | " | " | " | CO—⟨2-NO₂-phenyl⟩ |
| 192 | 2'-Chloro-4'-trifluoromethylphenyl | " | " | " | SO₂CH₃ |
| 193 | 2'-Chloro-4'-trifluoromethylphenyl | " | " | " | SO₂CF₃ |
| 194 | 2'-Chloro-4'-trifluoromethylphenyl | " | " | " | SO₂NHCH₃ |
| 195 | 2'-Chloro-4'-trifluoromethylphenyl | " | " | " | SO₂NH—i-propyl |
| 196 | 2'-Chloro-4'-trifluoromethylphenyl | " | " | " | SO₂NH(CH₃)₂ |
| 197 | 2'-Chloro-4'-trifluoromethylphenyl | " | " | " | CONHCH₃ |
| 198 | 2'-Chloro-4'-trifluoromethylphenyl | " | " | " | CON(CH₃)₂ |
| 200 | 2'-Chloro-4'-trifluoromethylphenyl | " | " | S | CNHCH₃<br>\|\|<br>O |
| 201 | 2'-Chloro-4'-trifluoromethylphenyl | " | " | " | CN(CH₃)₂<br>\|\|<br>O |
| 202 | 2'-Chloro-4'-trifluoromethylphenyl | " | " | O | CN(C₂H₅)₂<br>\|\|<br>O |
| 204 | 2'-Chloro-4'-trifluoromethylphenyl | " | " | " | Si(C₂H₅)₃ |
| 205 | 2'-Chloro-4'-trifluoromethylphenyl | " | " | " | Si(CH₃)₂(C₄H₉-n) |
| 206 | 2'-Chloro-4'-trifluoromethylphenyl | Br | " | " | Si(CH₃)₃ |
| 207 | 2'-Chloro-4'-trifluoromethylphenyl | Cl | " | " | Si(CH₃)₃ |
| 208 | 2'-Chloro-4'-trifluoromethylphenyl | CN | " | " | Si(CH₃)₃ |
| 209 | 2'-Chloro-4'-trifluoromethylphenyl | NO₂ | " | " | O<br>\|\|<br>P(OC₂H₅)₂ |
| 211 | 2'-Chloro-4'-trifluoromethylphenyl | " | " | S | O  S—i-C₃H₇<br>\|\|  /<br>P<br>\\<br>OC₂H₅ |
| 215 | 2'-Chloro-4'-trifluoromethylphenyl | " | S | S | —(CH₂)₃— |
| 217 | 2',4'-Dichlorophenyl | " | CN | O | H |
| 218 | 2',4'-Dichlorophenyl | " | H | " | C(CH₃)₃ |

-continued

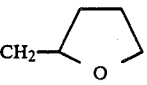

| Compound no. | $Z_3 = D$ | Y | $Z_4$ | X | A |
|---|---|---|---|---|---|
| 219 | 2',4'-Dichlorophenyl | " | " | " | Benzyl |
| 220 | 2',4'-Dichlorophenyl | " | " | " | 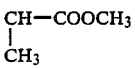 |
| 221 | 2',4'-Dichlorophenyl | " | " | S | H |
| 222 | 2',4'-Dichlorophenyl | " | " | " | $CH_3$ |
| 223 | 2',4'-Dichlorophenyl | " | " | $SO_2$ | $CH_3$ |
| 224 | 2',4'-Dichlorophenyl | " | " | S | Benzyl |
| 225 | 2',4'-Dichlorophenyl | " | " | O | $CH_2COOCH_3$ |
| 226 | 2',4'-Dichlorophenyl | " | " | " | $CH_2COOC_{18}H_{37}$ |
| 227 | 2',4'-Dichlorophenyl | " | " | " | CH—$COOCH_3$<br>\|<br>$CH_3$ |
| 228 | 2',4'-Dichlorophenyl | " | " | " | $CH_2CH_2COOC_{12}H_{25}$ |
| 229 | 2',4'-Dichlorophenyl | " | " | " | $CH_2CH_2COOC_{18}H_{37}$ |
| 231 | 2',4'-Dichlorophenyl | " | " | S | $CH_2COOC_{18}H_{37}$ |
| 232 | 2',4'-Dichlorophenyl | " | " | " | CH—$COOCH_3$<br>\|<br>$CH_3$ |
| 233 | 2',4'-Dichlorophenyl | " | " | " | $CH_2CH_2COOC_{18}H_{37}$ |
| 234 | 2',4'-Dichlorophenyl | " | " | " | $CH_2CH_2COOC_{12}H_{25}$ |
| 235 | 2',4'-Dichlorophenyl | " | " | $SO_2$ | $CH_2COOCH_3$ |
| 236 | 2',4'-Dichlorophenyl | " | " | SO | $CH_2COOCH_3$ |
| 237 | 2',4'-Dichlorophenyl | " | " | $SO_2$ | $CHCOOCH_3$<br>\|<br>$CH_3$ |
| 238 | 2',4'-Dichlorophenyl | " | " | SO | CH—$COOCH_3$<br>\|<br>$CH_3$ |
| 239 | 2',4'-Dichlorophenyl | " | " | O | 4-F—phenyl |
| 240 | 2',4'-Dichlorophenyl | " | " | S | 4-Methoxyphenyl |
| 252 | 2',4'-Dichlorophenyl | " | " | O | $SO_2N(CH_3)_2$ |
| 254 | 2',4'-Dichlorophenyl | " | " | " | $CN(CH_3)_2$<br>\|\|<br>O |
| 255 | 2',4'-Dichlorophenyl | " | " | " | $Si(CH_3)_3$ |
| 256 | 2',4'-Dichlorophenyl | " | " | " | $Si(C_2H_5)_3$ |
| 257 | 2',4'-Dichlorophenyl | " | " | " | S<br>\|\|<br>$P(OC_2H_5)_2$ |
| 262 | 2',4'-Dibromophenyl | " | " | " | $CH_2COOCH_3$ |
| 264 | 2',4'-Dibromophenyl | " | " | S | $CH_2CH_2COOC_{12}H_{25}$ |
| 265 | 2',4'-Dibromophenyl | " | " | " | $CH_2COOC_{18}H_{37}$ |
| 266 | 2',4'-Dibromophenyl | " | " | " | $CH_2CH_2COOC_{18}H_{37}$ |
| 270 | 2',4'-Dibromophenyl | " | " | O | $SO_2NHCH_3$ |
| 271 | 2',4'-Dibromophenyl | " | " | " | $Si(CH_3)_3$ |
| 274 | 2'-Chloro-4'-methylphenyl | " | " | " | $CH_2COOCH_3$ |
| 276 | 2'-Chloro-4'-methylphenyl | " | " | " | $Si(CH_3)_3$ |
| 279 | 2'-Methyl-4'-chlorophenyl | " | " | " | $CH_2COOCH_3$ |
| 283 | 2'-Chloro-4'-methoxyphenyl | " | " | " | $CH_2COOCH_3$ |
| 286 | 2'-Bromo-4'-chlorophenyl | " | " | S | $CH_2COOCH_3$ |
| 288 | 2'-Chloro-4'-fluorophenyl | " | " | " | $CH_2COOCH_3$ |
| 290 | 4'-Fluorophenyl | " | " | " | $CH_2COOCH_3$ |
| 297 | 2',4',6'-Trichlorphenyl | " | " | " | $CH_2COOCH_3$ |
| 298 | 2',6'-Dichloro-4'-trifluoromethylphenyl | " | " | " | $CH_2COOCH_3$ |
| 300 | 2'-Chloro-4-trifluoromethoxyphenyl | " | " | O | $CH_2COOCH_3$ |
| 302 | 2'-Chloro-4-trifluoromethoxyphenyl | " | " | S | $CH_2COOC_{18}H_{37}$ |
| 303 | 2'-Chloro-4-trifluoromethoxyphenyl | " | " | $SO_2$ | $CH_2COOCH_3$ |
| 305 | 2'-Chloro-4'-trifluorothiomethylphenyl | " | H | S | $CH_2COOCH_3$ |
| 306 | 2'-Chloro-4'-trifluorothiomethylphenyl | " | " | O | $CH_2COOCH_3$ |
| 307 | 2'-Chloro-4'-difluorochlormethylphenyl | " | " | S | $CH_2COOCH_3$ |
| 308 | 2'-Chloro-4'-difluorochlormethylphenyl | " | " | O | $CH_2COOCH_3$ |

-continued

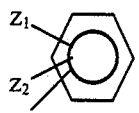

| Compound no. | $Z_3 = D$ | Y | $Z_4$ | X | A |
|---|---|---|---|---|---|
| 309 | 2'-Chloro-4'-trifluorosulfonylphenyl | " | " | S | $CH_2COOCH_3$ |
| 310 | 2'-Chloro-4'-trifluorosulfonylphenyl | " | " | O | $CH_2COOCH_3$ |
| 311 | 3'-Methylphenyl | " | " | S | $CH_2COOCH_3$ |
| 312 | 3'-Methylphenyl | " | " | O | $CH_2COOCH_3$ |
| 313 | 2'-Nitro-4'-trifluoromethylphenyl | H | " | S | $CH_2COOCH_3$ |
| 314 | 2'-Nitro-4'-trifluoromethylphenyl | " | " | O | $CH_2COOCH_3$ |
| 315 | 2'-Nitro-4'-trifluoromethylphenyl | $NO_2$ | " | S | $CH_2COOCH_3$ |
| 316 | 2'-Nitro-4'-trifluoromethylphenyl | " | " | O | $CH_2COOCH_3$ |
| 317 | 3',5'-Dichlorophenyl | " | " | S | $CH_2COOCH_3$ |
| 318 | 3',5'-Dichlorophenyl | " | " | O | $CH_2COOCH_3$ |
| 319 | 3',5'-Dimethylphenyl | " | " | S | $CH_2COOCH_3$ |
| 320 | 3',5'-Dimethylphenyl | " | " | O | $CH_2COOCH_3$ |

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably from 0.5 to 90, wt% of active ingredient.

The active ingredients are applied, for instance by watering, scattering, dusting, spraying or atomizing, to the plants or soil, by coating plants, or by introducing them into the irrigation water.

EXAMPLE I 90 parts by weight of compound 1 was mixed with 10 parts by weight of N-methyl-α-pyrrolidone. A mixture was obtained suitable for application in the form of very fine drops.

EXAMPLE II 10 parts by weight of compound 2 was dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

EXAMPLE III 20 parts by weight of compound 2 was dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

EXAMPLE IV 20 parts by weight of compound 3 was dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide with 1 mole of castor oil.

EXAMPLE V 80 parts by weight of compound 1 was well mixed with 3 parts by weight of the sodium salt of diisobutyl-naphthalene-α-sulfonic acid, 10 parts by weight of the sodium salt of a lignin-sulfonic acid obtained from a sulfite waste liquor, and 7 parts by weight of powdered silica gel, and triturated in a hammer mill.

EXAMPLE VI 5 parts by weight of compound 1 was intimately mixed with 95 parts by weight of particulate kaolin. A dust was obtained containing 5% by weight of the active ingredient.

EXAMPLE VII 30 parts by weight of compound 1 was intimately mixed with a mixture consisting of 92 parts by weight of powdered silica gel and 8 parts by weight of paraffin oil which had been sprayed onto the surface of this silica gel. A formulation of the active ingredient was obtained having good adherence.

EXAMPLE VIII 40 parts by weight of compound 1 was intimately mixed with 10 parts of the sodium salt of a phenolsulfonic acid-urea-formaldehyde condensate, 2 parts of silica gel and 48 parts of water to give a stable, aqueous dispersion.

EXAMPLE IX 20 parts of compound 1 was intimately mixed with 12 parts of rhe calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion was obtained.

The active ingredients may be applied either pre- or post-emergence. They are, however, preferably applied after emergence of the unwanted plants, both on cropland and uncropped land. If certain crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient which is applied depends on the season and the growth stage, and varies from 0.025 to 15 kg/ha and more.

The influence of various representatives of the novel herbicidal diphenyl ethers on the growth of unwanted plants is demonstrated in greenhouse experiments.

The vessels employed were plastic flowerpots having a volume of 300 cm³, and which were filled with a sandy loam containing about 1.5% humus. The seeds of the test plants were sown shallow, and separately, according to species.

In the preemergence treatment, the active ingredients were immediately applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. Where rice was used for the postemergence treatment, the substrate was enriched with peat. For this treatment, either plants which had been sown directly in the pots and grown there were selected, or plants which had been grown separately as seedlings and transplanted to the experiment vessels a few days before treatment. Application rates for postemergence treatment vary from active ingredient to active ingredient. They were in each case 0.125, 0.25 and 0.5 kg/ha, and, in the case of some compounds, 3.0 kg/ha. No cover was placed on the vessels in this treatment.

The following prior art compounds were used for comparison purposes at a rate of 0.125 kg/ha:

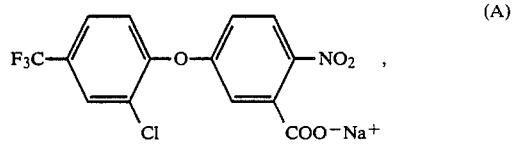
(A)

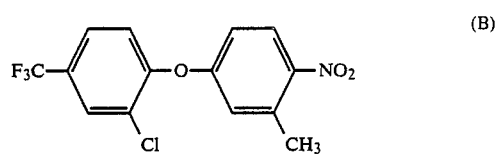
(B)

and

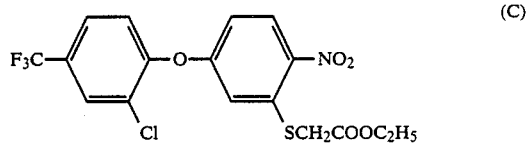
(C)

The pots were set up in the greenhouse—species from warmer areas at from 20° to 35° C., and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The greenhouse experiments showed that novel compounds nos. 321, 322, 96, 10, 268, 269, 203, 11, 248, 18, 175, 13, 230, 94, 326 and 15 had, on preemergence application at rate of 3.0 kg/ha, a very good herbicidal action.

In investigations into the herbicidal action on postemergence application in the greenhouse, compounds nos. 280, 275, 284, 292, 156 and 295 proved, at 3.0 kg/ha, to have a good action.

In further investigations into the herbicidal action on postemergence application in the greenhouse, compounds nos. 5, 14, 263, 148, 120, 153, 230, 324, 321, 140 and 142 at 0.25 kg/ha, and compounds nos. 1, 87, 13, 4, 16, 101, 175, 214, 216, 96, 104 and 325 at 0.5 kg/ha had a very good action on broadleaved unwanted plants.

In investigations into selective herbicidal action on postemergence application in the greenhouse, compound no. 153 had, at 0.125 kg/ha, a superior herbicidal action on various broadleaved weed species and was better tolerated by wheat (with at most slight and temporary leaf scorching) than the prior art comparative compound B at the same rate.

The greenhouse experiments also revealed that compound no. 104, applied postemergence at 0.125 kg/ha, had a better herbicidal action than comparative agent A and was better tolerated by wheat.

The greenhouse experiments also showed that compounds nos. 5 and 16, on foliage application at 0.125 kg/ha, had a herbicidal action similar to that of prior art comparative agent C. However, novel compounds 5 and 16 were better tolerated by groundnuts than comparative compound C, and compound no. 5 was also better tolerated by wheat.

The novel compounds have a selective herbicidal action in numerous crops, for example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape seed |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the novel diphenyl ethers may be mixed among themselves, or mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenyl-carbamates, thiolcarbamates, halocarboxylic acids, triazines, amides, ureas, other diphenyl ethers, triazinones, uracils, benzofuran derivatives, cyclohexan-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone 5-methoxy-4-chloro-2-(3-trifluoromethylphenyl)-3(2H)-pyridazinone
5-amino-4-bromo-2-(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-carbamate
methyl-N-(3-(N'-3-chloro-4-fluorophenylcarbamoyloxy)-phenyl)-carbamate
ethyl-N-[3-N'-(3-chloro-4-fluorophenylcarbamoyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenyl carbamate
ethyl N-3-(2'-methylphenoxycarbonylamino)-phenyl carbamate
methyl N-3-(4'-fluorophenoxycarbonylamino)-phenyl thiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.2.1]-heptylthiolcarbamate
S-(2,3-dichlorallyl)-2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methylα-chloro-β-(4-chlorophenyl)-propionate
methylα,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(40'-chlorophenoxy)-phenoxy]-propionate methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt,
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H,1,2,4-triazol-1-yl)-butan-2-one
N,N-diallylchloroacetamide
N-isopropyl-2-chloroacetanilide
N-(1-methylprop-2-ynyl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazol-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(2-n-propoxyethyl)-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)

2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-($\alpha,\alpha$-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(3-$\alpha,\alpha,\beta,\beta$-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl $\alpha$-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithioate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)

succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethylphenyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methyl-pyrazole
3-anilino-4-methoxycarbonyl-5-methylpyrazole
3-tert.butylamino-4-methoxycarbonyl-5-methyl-pyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxyamino)-butylidene]-5-(2-ethylthio-propyl)-3-hydroxy-cyclohex-2-en-1-one (salts)
2-[1-(N-ethoxamino)-butylidene]-5-(2-phenylthio-propyl)-3-hydroxy-cyclohex-2-en-1-one (salts)
ethyl-4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4-nitrophenyl ether (salts)
4,5-dimethoxy-2-(3-α,α,β-trifluoro-β-bromoethoxy-phenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-pyridine It may also be useful to apply the novel compounds, either on their own or combined with other herbicides, in admixture with other crop protection agents, e.g., agents for combating pests or phytopathogenic fungi or bacteria. The compounds may also be mixed with, solutions of mineral salts used to remedy nutritional or trace element deficiencies. Non-phytotoxic oils and oil concentrates may also be added.

We claim:

1. A substituted diphenyl ether of the formula

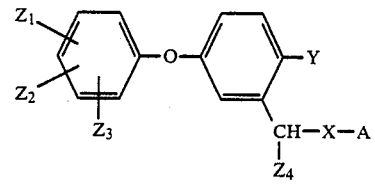

where $Z_1$ is 2-chloro, $Z_2$ is 4-trifluoromethyl, $Z_3$ is hydrogen, $Z_4$ is hydrogen, cyano, $C_1$-$C_4$-alkyl, $C_1$-$C_4$-alkoxy, acetoxy or $C_1$-$C_4$-alkylmercapto, Y is chlorine, bromine, cyano or nitro, X is oxygen, sulfur, sulfinyl or sulfonyl, and A is $C_1$-$C_6$-alkyl, $C_1$-$C_4$ alkyl substituted by tetrahydrofuryl;

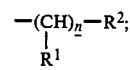

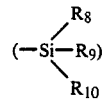

where $R_8$, $R_9$ and $R_{10}$ are identical or different and are methyl, ethyl, n-propyl or n-butyl;

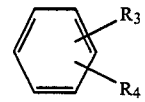

where $R^3$ is hydrogen and $R^4$ is;

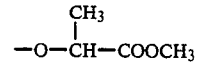

or benzyl substituted by chlorine; where $R^1$ is hydrogen, methyl, ethyl or n-propyl, $R^2$ is cyano, methoxy, ethoxy,

where B is OH, ONa, OCH$_3$, OC$_2$H$_5$, O—i—C$_3$-H$_7$ or O—(C$_4$-C$_{20}$)-alkyl, O-phenyl, fluoro-substituted phenoxy, —NH$_2$, —NH(C$_1$-C$_4$)-alkyl or —N((C$_1$-C$_4$)-alkyl)$_2$ and n is 1, 2, or 3.

2. A substituted diphenyl ester as set forth in claim 1, wherein A is

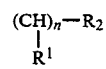

wherein $R^1$ is hydrogen, methyl, ethyl or n-propyl and $R_2$ is

where B is OH, ONa, OCH$_3$, OC$_2$H$_5$, O—i—C$_3$H$_7$ or O—(C$_4$-C$_{20}$)-alkyl, O-phenyl, fluoro-substituted phenoxy, —NH$_2$, —NH—C$_1$–C$_4$-alkyl or —N(C$_1$–C$_4$-alkyl)$_2$ and n is 1, 2 or 3.

3. A substituted diphenyl ether selected from the group consisting of methyl 3-(2′-chloro-4′-trifluoromethylphenoxy)-benzylthioacetate, methyl 3-(2′-chloro-4′-trifluoromethylphenoxy)-6-nitrobenzoxyacetate, methyl 3-(2′-chloro-4′-trifluoromethylphenoxy)-6-nitrobenzylthioacetate, methyl 3-(2′-chloro-4′-trifluoromethylphenoxy)-6-bromobenzylthioacetate,

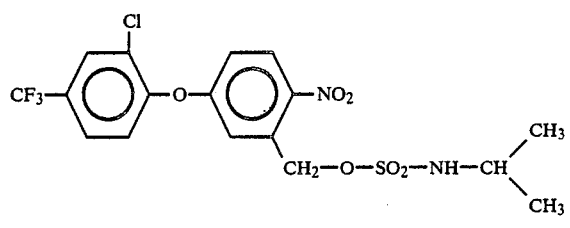

and

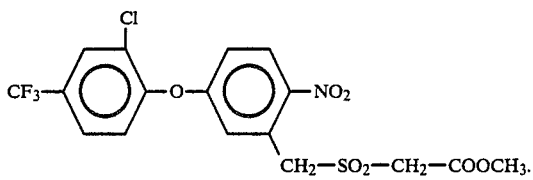

4. A compound represented by the formula:

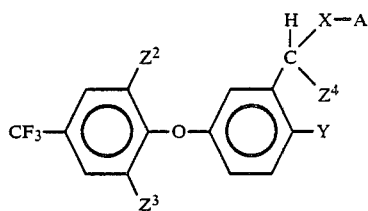

wherein
Z$^2$ and Z$^3$ are hydrogen or halogen provided that at least one of Z$^2$ or Z$^3$ is halogen; 'Y is nitro, halogen or cyano;
A is C$_1$–C$_4$-alkyl, X is oxygen; and
Z$^4$ is C$_1$–C$_4$-alkoxy.

5. A process for combating unwanted plants, wherein the plants or the soil are treated with an effective amount of a diphenyl ether of the formula I as defined in claim 1.

6. The process of claim 5, wherein A is

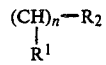

wherein R$^1$ is hydrogen, methyl, ethyl or n-propyl and R$_2$ is

where B is OH, ONa, OCH$_3$, OC$_2$H$_5$, O—i—C$_3$H$_7$ or O—(C$_4$–$_{C20}$)-alkyl, O-phenyl, fluoro-substituted phenoxy, —NH$_2$, —NH—C$_1$–C$_4$-alkyl or —N(C$_1$–C$_4$-alkyl)$_2$ and n is 1, 2 or 3.

* * * * *